(12) United States Patent
Gerg et al.

(10) Patent No.: US 8,460,324 B2
(45) Date of Patent: Jun. 11, 2013

(54) HIGH SPEED PNEUMATIC VITRECTOMY CONTROL

(75) Inventors: James Gerg, Lake Forest, CA (US); Ernesto Flores, Irvine, CA (US); Fred Lee, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 798 days.

(21) Appl. No.: 12/424,295

(22) Filed: Apr. 15, 2009

(65) Prior Publication Data
US 2009/0259242 A1 Oct. 15, 2009

Related U.S. Application Data

(60) Provisional application No. 61/124,202, filed on Apr. 15, 2008.

(51) Int. Cl.
*A61F 9/007* (2006.01)

(52) U.S. Cl.
USPC .......................................... 606/166

(58) Field of Classification Search
USPC ......... 606/166, 169; 604/22; 83/639.1–639.5, 83/639.7
See application file for complete search history.

(56) References Cited

U.S. PATENT DOCUMENTS

| 5,417,246 A * | 5/1995 | Perkins et al. ................. 137/870 |
| 2003/0195538 A1* | 10/2003 | Wang et al. ................... 606/169 |

* cited by examiner

*Primary Examiner* — Ryan Severson
(74) *Attorney, Agent, or Firm* — Abbott Medical Optics Inc.

(57) ABSTRACT

A method and system for controlling the cutting speed of a cutting device employable in an ocular surgical procedure is provided. The apparatus includes a control module, a variable gas pressure regulator arrangement configured to receive gas from a gas pressure supply, wherein the variable pressure regulator arrangement is connected to the control module and the control module is configured to regulate gas received from the gas pressure supply, and an accumulator configured to store gas received from the variable gas regulator arrangement at a selected gas pressure. Gas at the desired pressure is delivered from the accumulator to the cutting device. The gas may be air, and the variable gas pressure arrangement may include a single variable pressure regulator or multiple pressure regulators which typically are not variable with respect to the pressure delivered.

8 Claims, 9 Drawing Sheets

HIGH SPEED PNEUMATIC VITRECTOMY CONTROL

This application claims priority to U.S. Provisional Application No. 61/124,202 filed on Apr. 15, 2008, the entire contents of which are hereby incorporated by reference in its entirety for all purposes as if fully set forth herein.

BACKGROUND OF THE INVENTION

1. Field of the Invention

The present invention relates generally to the field of surgical repair of retinal disorders, and more specifically to pneumatic Vitrectomy cutter power delivery during ophthalmic procedures such as the removal of vitreous gel.

2. Description of the Related Art

Vitrectomy surgery has been successfully employed in the treatment of certain ocular problems, such as retinal detachments, resulting from tears or holes in the retina. Vitrectomy surgery typically involves removal of vitreous gel and may utilize three small incisions in the pars plana of the patient's eye. These incisions allow the surgeon to pass three separate instruments into the patient's eye to affect the ocular procedure. The surgical instruments typically include a vitreous cutting device, an illumination source, and an infusion port. Current vitreous cutting devices may involve a "guillotine type action" where a small knife is used to remove the vitreous gel. Vitreous cutters are available in either electric or pneumatic form. Today's electric cutters may operate within a range of speeds typically between 750-2500 cuts-per-minute (CPM) where pneumatic cutters may operate within a range of speeds between speeds 400-2100 CPM. The surgeon or practitioner may adjust to control, by selecting or varying, the pneumatic vitrectomy surgical instrument cutting speed, i.e. the cutting device within the handpiece, sufficient to perform different activities during the corrective procedure. Corrective procedures may include: macular degeneration, retinal detachment, macular pucker, and eye injuries.

The cutting device within the handpiece requires precise control of the speed of the cutting blade. Today's systems typically employ a constant or fixed frequency control signal to open and close the valve resulting in fixed cyclic valve timing and a fixed, relatively rapid cutting speed. Input supply pressure is varied to achieve a desired cutting speed.

Designs based on varying the input supplying pressure to control the speed or rate of cutting are limited by how quickly the air volume in the cutter body and the associated tube set may be pressurized to reach the minimum peak pressure required to advance the cutter to a cut position and then vent to reach the minimum residual pressure to allow the spring-loaded cutter to return to a retracted position. Current pneumatic designs are limited to cutting speeds within a range of approximately 400 to 2100 cuts per minute.

Today's vitrectomy surgical systems require a wide range of selectable cutting speeds and highly accurate control of the amount of air pressure supplied to ensure proper instrument handpiece control and safe use in an operating theater. It may be beneficial in certain circumstances to offer the surgeon variations in cutting speeds, controllability, and options related to performing a vitrectomy procedure. Based on the foregoing, it would be advantageous to provide a system that enables pneumatic cutting functionality at cutting speeds at or higher than achievable with today's designs vitrectomy surgical instrument systems with varying options in effectuating the highest desired cutting speeds.

SUMMARY OF THE INVENTION

According to one aspect of the present design, there is provided a method for controlling a cutting device employed by an ocular surgical system, such as a vitrectomy surgical system. The method comprises supplying gas pressure to a variable gas pressure arrangement, providing for selectability of a desired gas pressure value from the variable gas pressure arrangement based on a desired cutting speed for the cutting device, storing gas at approximately the desired gas pressure value in an accumulator, and delivering gas pressure from the accumulator to the cutting device. The gas may be air, and the variable gas pressure arrangement may include a single variable pressure regulator or multiple pressure regulators which typically are not variable with respect to the pressure delivered.

According to a second aspect of the present design, there is provided an apparatus configured to control cutting speed of a cutting device employable in an ocular surgical procedure. The apparatus comprises a control module, a variable pressure regulator arrangement comprising two or more air pressure regulators sources configured to receive gas from a gas pressure supply, wherein the variable pressure regulator arrangement is connected to the control module and the control module is configured to regulate gas received from the gas pressure supply, and an accumulator configured to store gas received from the variable regulator arrangement at a selected gas pressure. Air volume is selectively delivered from the accumulator to the cutting device.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE INVENTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design provides a system and method for high-speed pneumatic vitrectomy control that may be used to precisely set and vary the cutting speed of the associated cutting blade mechanism over a wide range of operational speeds.

While the present design may be employed in various systems involving cutting blades, it is illustrated herein in an exemplary phacoemulsification—vitrectomy—diathermy system. It is to be understood that any type of system having supply air pressure control issues may benefit from the design presented herein, and such a design is not limited to a phacoemulsification—vitrectomy—diathermy system or even a medical system.

The present design is directed to accurate, reliable, and efficient control of the forward and backward reciprocating motion cutting speed of the blade in a pneumatic vitrectomy handpiece used in a medical instrument system. The present design will be discussed herein with a particular emphasis on a medical or hospital environment, where a surgeon or health care practitioner performs. For example, an embodiment of the present design is a phacoemulsification surgical system that comprises an integrated high-speed control module for the vitrectomy handpiece. The surgeon or practitioner may adjust or set the blade speed via a graphical user interface (GUI) module, a switch located on the handpiece, or a foot pedal switch to control the high-speed pneumatic vitrectomy handpiece.

System

Figure 1A:
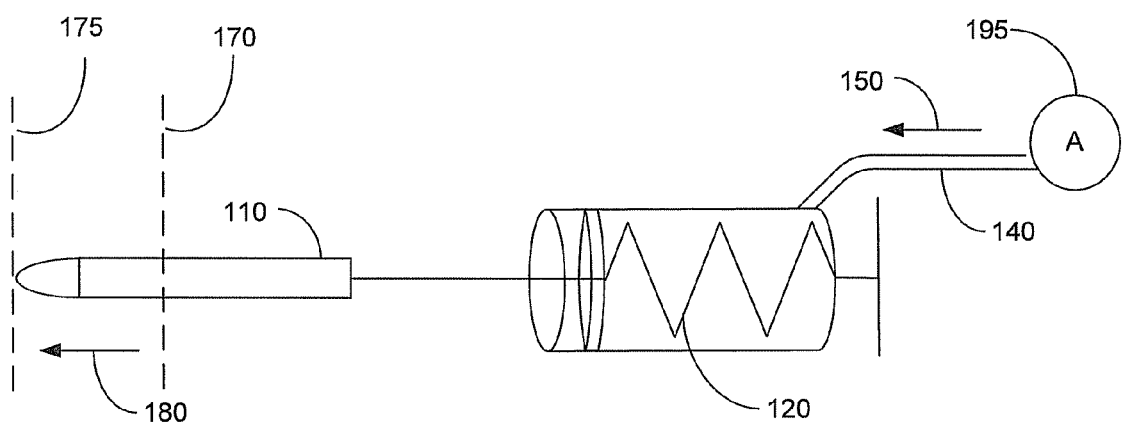
FIG. 1A is high-level conceptual block diagrams to illustrate a common vitrectomy system's pneumatic cutting mechanism, located within a surgical handpiece, with the pneumatic cutting mechanism in a "cut" or "forward" position.
Figure 1B:
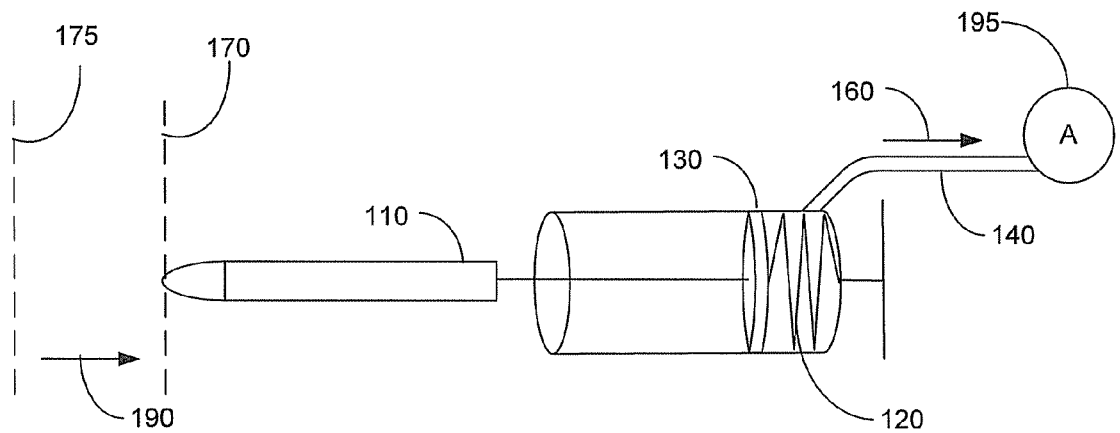
FIG. 1B is high-level conceptual block diagrams to illustrate a common vitrectomy system's pneumatic cutting mechanism, located within a surgical handpiece, with the pneumatic cutting mechanism in an "initial" or "backward" position.

FIGS. 1A and 1B are high-level conceptual block diagrams to illustrate a common vitrectomy system's pneumatic cutting mechanism located within a surgical handpiece. FIG. 1A shows the pneumatic cutting mechanism in the "cut" or "forward" position, while FIG. 1B shows the pneumatic cutting mechanism in the "initial" or "backward" position. Referring to FIG. 1A, construction of today's pneumatic cutter devices typically involve a blade 110 positioned to work or operate against a spring 120 by inflating and deflating a bladder 130 configured to move blade 110 by 'pushing' blade 110 forward to a forward position at 175 when bladder 130 is inflated and 'pulling' blade 110 backward by the energy stored in spring 120 to its resting position or initial position 170 when bladder 130 is deflated. The desired cutting speed may be realized by filling and emptying bladder 130 in a cyclical manner through an air passage 140 arranged for receiving a pressurized air-burst in the direction indicated at point 150. The received pressurized air burst is then evacuated or vented in direction 160. Current designs are generally configured to cyclically inflate and deflate bladder 130 to move blade 110 in a forward direction 180 and backward direction 190, thus producing the desired cutting action. A combination input pressurized air supply and output air venting valve mechanism 195, or valve, is shown 195.

In order to control the speed of blade 110, currently available pneumatic designs typically use a control signal to open and close valve 195. Valve 195 may be configured to provide a pressurized airburst when the valve is open, i.e. control signal in the energized state, filling bladder 130 and venting the air within bladder 130 when the valve is closed, i.e. the control signal is in the de-energized state, to empty the bladder. Increasing the frequency of the control signal cycling rate, which produces a shorter pressurized air burst time, generally results in an increased cutting speed, or an increased number of cuts-per-minute as observed at the knife. A subsequent decrease in control signal cycling rate generally produces a slower or decreased cutting speed.

Figure 2A:
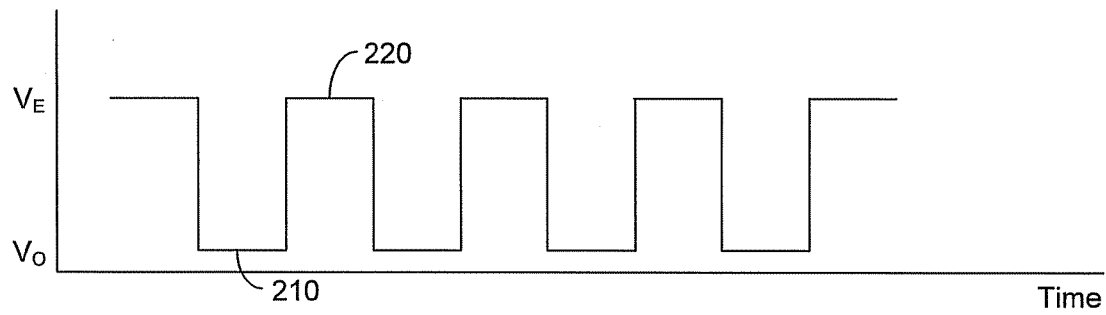
FIG. 2A is a graph illustrating a typical cyclical control signal used for opening and closing a valve by setting the valve to either an energizing or a de-energizing state.
Figure 2B:
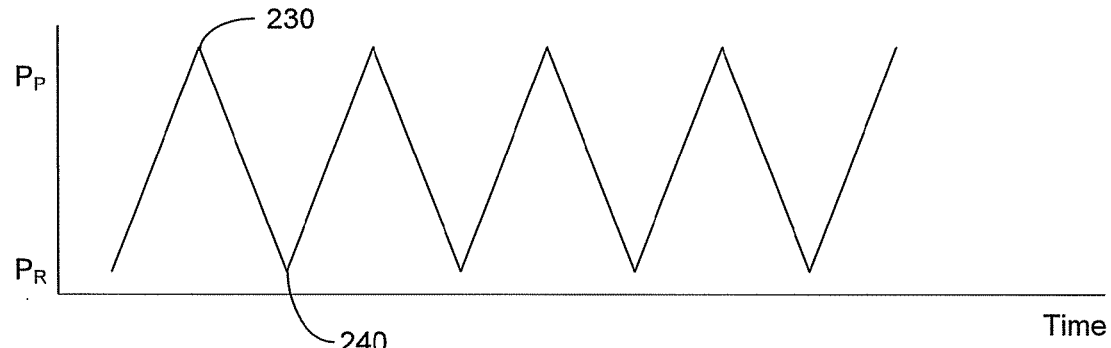
FIG. 2B is a graph illustrating an output pressure waveform resulting from the control signal illustrated in FIG. 2A.

An example control signal to instruct the opening and closing of valve 195 associated with air passage 140 is shown in FIG. 2A. The control signal illustrated in FIG. 2A may cycle between a valve-off ($V_O$) at point 210 to a valve-on ($V_E$) at point 220, or provide a valve-energized instruction at a predetermined cycling rate, thereby effectuating the desired cutting speed. FIG. 2B illustrates an example pressure waveform resulting from the application of the control signal shown in FIG. 2A. The waveform is shown to have a constant rise in pressure up to a peak pressure ($P_P$) at 230 when the valve is energized. A subsequent drop in pressure to a residual pressure ($P_R$) at point 240 occurs when the valve is de-energized. The cycling in pressure, for controlling the blade forward and backward reciprocating movements, as illustrated by the waveform shown in FIG. 2B, may produce a specific cutting speed for blade 110 in terms of cuts-per-minute.

In addition, today's pneumatic cutter designs may be configured with a speed control device to select and vary the rate the blade mechanism moves forward and backward to effect cutting. In these designs, the speed of the blade may involve changing or varying time or duration the control signal provides to the valve. By increasing the time valve 195 is open and closed, the resultant blade speed is reduced. Likewise, decreasing the time valve 195 is open and closed will cause the blade speed to increase.

Figure 2C:
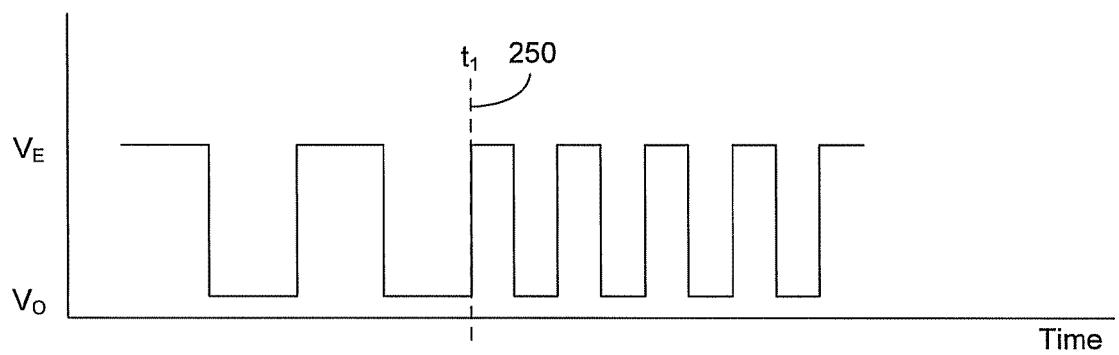
FIG. 2C is a graph illustrating the cyclical control signal applied to a valve where at a specific instance in time the frequency is increased.
Figure 2D:
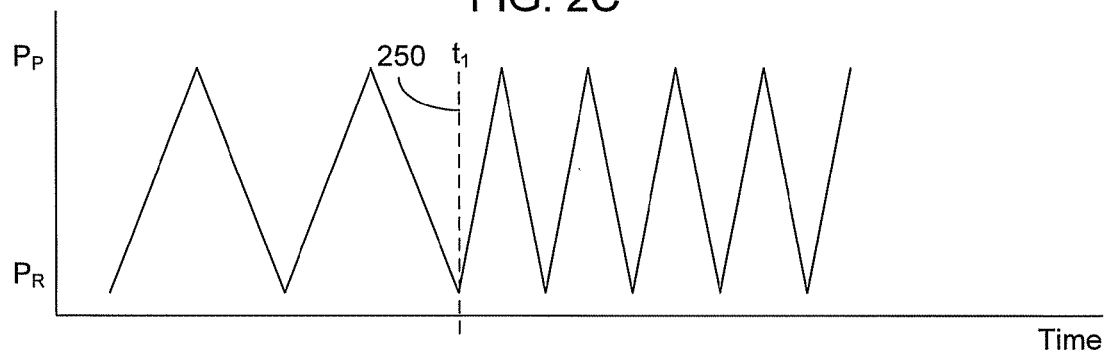
FIG. 2D is a graph illustrating a pressure waveform resulting from the change in the cyclical control signal frequency as illustrated in FIG. 2C.

An example of a control signal for controlling the filling and emptying of air in bladder 130 with an increase in cycle time is illustrated in FIG. 2C. Before time $t_1$ at 250, the control signal cyclic frequency is set at a lower rate than after time $t_1$ to illustrate the surgeon selecting an increase in cutting speed at time $t_1$ during a surgical procedure. FIG. 2D illustrates an example pressure waveform resulting from the application of the control signal shown in FIG. 2C. This pressure waveform reflects the control signal change that occurred at time t1 at 250, and may drive blade 110 at a faster rate.

Figure 3A:
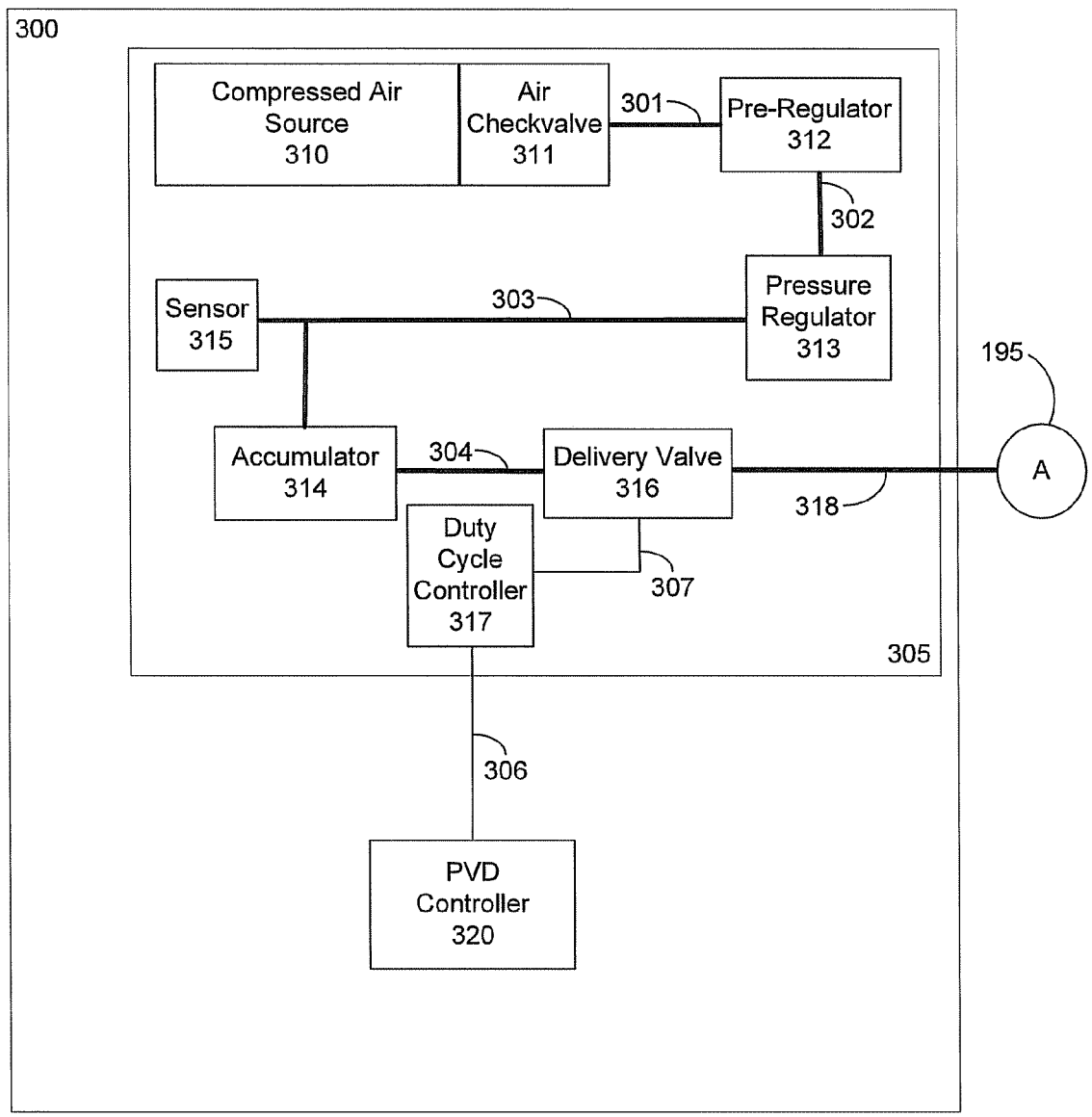
FIG. 3A is a block diagram illustrating components and devices for a pneumatic vitreous cutting module integrated within a phacoemulsification machine.

The pneumatic vitrectomy handpiece is used in connection with a phaco-vitrectomy module, illustrated in FIG. 3A, forming part of a phacoemulsification machine, and may include a guillotine type cutter pneumatically driven to either an open or closed position. Opening and closing occurs via air pressure provided inside a flexible line or delivery line between the cutter and a pneumatic driver. The pneumatic driver may include a pump configured to fill a small reservoir with compressed air at its maximum pressure capacity. The output of this reservoir is connected to a pressure regulator that may regulate the air pressure down to the level required by the cutter, as shown by peak $P_P$ and residual $P_R$ pressure in FIG. 2B. A smaller reservoir may be supplied or fed by the regulator output, forming the source for the delivery valve.

The electronic controller may be connected to the delivery valve and may provide instructions to produce a pulse width (in time) of pressurized air when the valve is open. The controller may be arranged to provide fixed pulses of pressurized air within the flexible line in a manner that drives the cutter. The electronic controller may use a fixed pulse timing control signal to instruct the delivery valve to open and close. The fixed timing, or fixed duration, control signal instructs the delivery valve to open and close in a constant cyclical manner. When the flexible line is at zero or near zero pressure, for example refer to residual pressure $P_R$ shown in FIG. 2B, the cutter is biased toward the initial or resting position. The cutter closes when the air pressure in the cutter delivery line exceeds a predetermined value between $P_R$ and $P_P$. When the delivery valve is off, the air in the cutter tubing is exhausted through the valve exhaust port. The cutter then returns to the initial position when the pressure in the delivery line decreases close to atmospheric pressure, i.e. $P_R$.

FIG. 3A is a block diagram illustrating components and devices for a Pneumatic Vitreous Cutting Module 305 integrated within a Phacoemulsification Machine 300. From FIG. 3A, a Compressed Air Source 310 and associated Air Check valve 311 may supply air pressure for Pneumatic Vitreous Cutting Module 305. The supply air pressure source may be provided by a pump, not shown, that may receive air at atmospheric pressure and forms a vacuum or pressure source. Compressed air is provided by the pump via Delivery Line 301 illustrated between Air Check valve 311 and Pre-Regulator 312. Check valve 311 is arranged with two ports and may allow air pressure to flow through in one direction, from Compressed Air Source 310 to Pre-Regulator 312. The pump may pump pressurized air into a high pressure chamber, not shown, which in turn provides high pressure air to Pre-Regulator 312 via Delivery Line 301. The high-pressure chamber, or compressed air source 310, may connect to the pump by a delivery line, not shown, and may provide a stable source of air at a higher pressure than the working pressure of the cutter.

Pre-Regulator 312 may provide a workable steady air pressure stream from which module 310 may supply air pressure for Pressure Regulator 313 via Delivery Line 302. Pressure Regulator 313 may be preset, such as at 18 psig, for example, and may be configured to provide air to Accumulator 314 at a low-steady safe operating pressure. Pressure Regulator 313 may connect to Compressed Air Source 310, e.g. high pressure chamber, by a delivery line and take input high pressure and regulate the air pressure to a lower value consistent with the operating pressure of the cutter handpiece. In this example Pressure Regulator 313 is set to 18 psig.

Accumulator 314 may operate as a working pressure chamber, and may receive pressured air at specific pressure and volume from Pressure Regulator 313 via Delivery Line 303. Sensor 315 may monitor the pressure coming from Pressure Regulator 313 by accessing Delivery Line 303. Sensor 315 may operate to determine the pressure in Delivery Line 303, located between Pressure Regulator 313 and Compressed Air Source 310 for the purpose of sensing the level of air pressure or amount of air pressure available for Accumulator 314 and notifying the host system if the value is too high or too low. Accumulator 314 may provide a specific amount of air pressure at a predetermined volume to Delivery Valve 316 via Delivery Line 304 so that no excess pressure is forced into the Cutter Tubing 318.

PVD (Phaco-Vitrectomy-Diathermy) Controller 320, which may provide a graphical user interface, computes a cut rate based on physician input and electronically provides the cut rate to Duty Cycle Controller 317 via communications Control Line 306. Control Line 306 drives Delivery Valve 316 at the specified fixed time cyclical pulse rate via communications Control Line 307. Although depicted as an integral unit, module 305 functionality may be realized by using an external unit to perform the same functionality as disclosed for the integral unit design. Delivery Valve 316 may open and close in response to the control signal provided from Duty Cycle Controller 317. Duty Cycle Controller 317 electronically controls the valves operating the regulated pressure and/or vacuum air sent to the cutter. The Duty Cycle Controller 317 may connect to Delivery Valve 316 to control Delivery Valve 316. The handpiece blade motion may move in a forward and backward reciprocating motion in response to the pressure waveform generated at 318.

During operation, Duty Cycle Controller 317 may operate Delivery Valve 316 to deliver a pulse of regulated air pressure to Cutter Tubing 318 and cutter (not shown). The pulses that drive the delivery valve 316 have a fixed width of sufficient duration to drive the cutter to the closed position throughout the entire range of operation. While the surgeon or practitioner may select variations in the pulse repetition frequency, once the selection is made, the pulse width, or width of each pulse, is uniform or constant during handpiece cutter operation.

Delivery Valve 316 is electronically controlled by Duty Cycle Controller 317 to transmit pressure in a fixed pulse width and opens and closes at a precise time to allow air at a specific pressure and volume to fill the Cutter Tubing 318 and operate the cutter. Delivery Valve 316 may connect to atmospheric pressure for purposes of venting Cutter Tubing 318. Duty Cycle Controller 317 may receive instructions from PVD Controller 320, and may communicate electronically via communications Control Line 307. Controller 320 may provide an electronic indication to Duty Cycle Controller 317 that originates with a user selected switch, such as a switch on the handpiece, graphical user interface, or a foot switch.

Figure 3B:
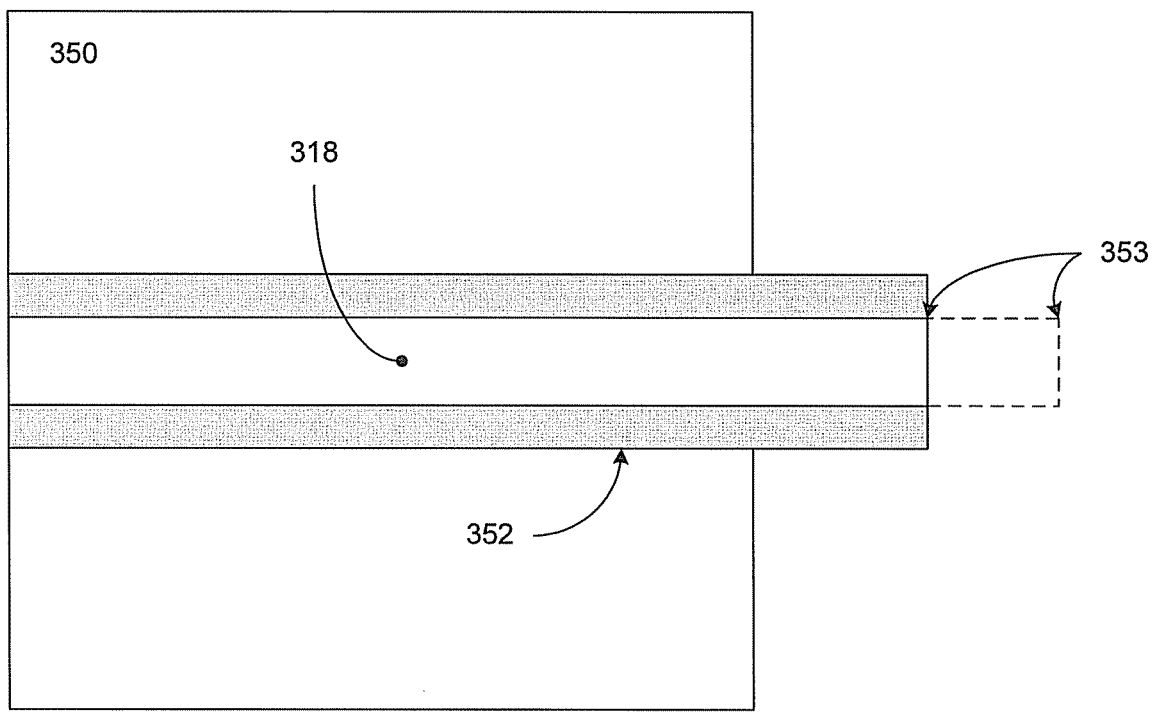
FIG. 3B illustrates a handpiece used in the vitrectomy procedure intended to be used with the variable pressure pneumatic vitrectomy control.

FIG. 3B illustrates a handpiece used in the vitrectomy procedure that may be operated with the variable pressure pneumatic vitrectomy control. From FIG. 3B, Cutter Tubing 318 is positioned within an outer passageway 352, and the handpiece 350 and pneumatics described above drive the end of cutter tubing 353 back and forth to cut vitreous material. The end of Cutter Tubing 318 current designs may involve a uniform inner and outer diameter with the remainder of the Cutter Tubing 318 where the inner and outer diameter of Cutter Tubing 318 is uniform along the entire length of Cutter Tubing 318, including the end of Cutter Tubing 318.

High Speed Pneumatic Vitrectomy Control

The present design provides a method for controlling a cutting device employed by an ocular surgical system, such as a vitrectomy surgical system. Gas pressure is provided to a variable gas pressure arrangement, providing for selectability of a desired gas pressure value from the variable gas pressure arrangement based on a desired cutting speed for the cutting device, storing gas at approximately the desired gas pressure value in an accumulator, and delivering gas pressure from the accumulator to the cutting device. The gas may be air, and the variable gas pressure arrangement may include a single variable pressure regulator or multiple pressure regulators which typically are not variable with respect to the pressure delivered.

Alternately, the design may be considered to include an apparatus configured to control cutting speed of a cutting device employable in an ocular surgical procedure. The apparatus comprises a control module, a variable pressure regulator arrangement comprising two or more air pressure regulators sources configured to receive gas from a gas pressure supply. The variable pressure regulator arrangement is connected to the control module and the control module is configured to regulate gas received from the gas pressure supply, and an accumulator configured to store gas received from the variable regulator arrangement at a selected gas pressure. Air volume is selectively delivered from the accumulator to the cutting device.

Figure 4:
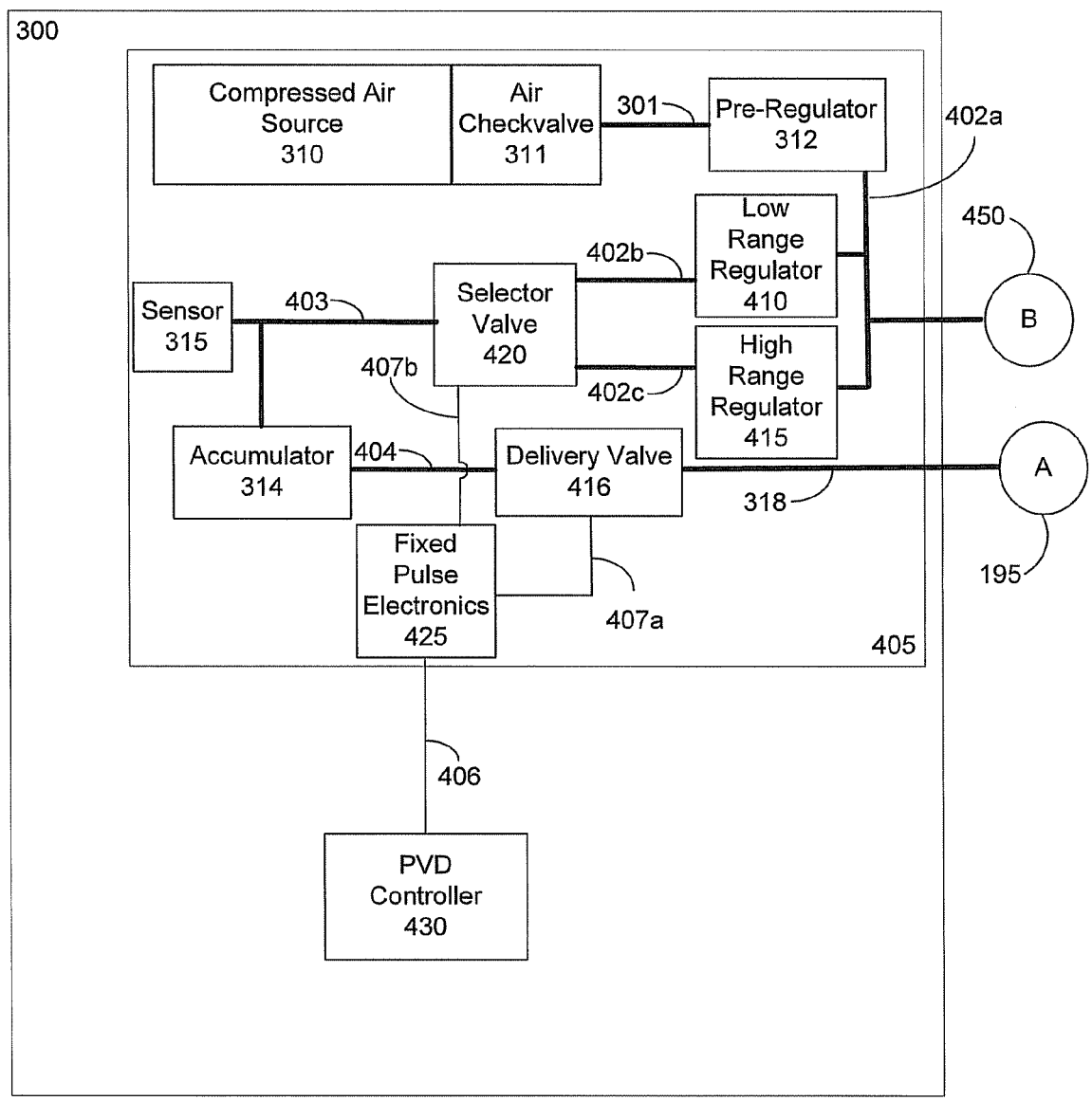
FIG. 4 is a block diagram illustrating components and devices for a high speed pneumatic vitreous cutting control module integrated within a phacoemulsification machine in accordance with one aspect of the present invention.

FIG. 4 is a functional block diagram of an exemplary fixed timing variable pressure pneumatic vitrectomy high-speed control module 405 illustrating an arrangement of major components and devices required to realize the present design. This arrangement may use the pressure/vacuum generation equipment configured within a system such as the Phacoemulsification System 300. The major difference between the present design and the previous example is the availability of more than one selectable air pressure source, where each available pressure source is set to a different predetermined value.

From FIG. 4, the present design may involve a source of compressed air, and may regulate down the compressed air, ready for use to drive the vitrectomy handpiece (i.e. cutter). In this example, Compressed Air Source 310 may provide compressed air to Pre-Regulator 312 in the same manner as previously described for the pneumatic vitrectomy control example. The present design may deliver compressed air from Pre-Regulator 312, via Delivery Line 402a, to a Low Range Regulator 410 and High Range Regulator 415 simultaneously. An input air pressure supply for each regulator is indicated as 'B' at 450. The Low Range Regulator 410 may be configured or preset to a value, for example at 18 psig, and the High Range Regulator 415 may be configured at 25 psig. A Selector Valve 420 device may receive air pressure from both the Low and High Range Regulators and may be configured to switch between the high and low pressure range based on control signals originating from Fixed Pulse Electronics 425 via communications Control Line 407b. Selector Valve 420 may switch the input source from High Range Regulator 415 to the Low Range Regulator based on the desired cutting speed selected by the surgeon or operator. In this arrangement, the present design may switch from a high-pressure input provided via Delivery Line 402c to a low-pressure input provided via Delivery Line 402b when high-speed cutting is selected. In this arrangement, for low-speed operation, the high-pressure input source is used and the low pressure during high-speed cutting. Fixed Pulse Electronics 425 may instruct Selector Valve 420 to pass air pressure received on Delivery Line 402c to Delivery Line 403.

In this example, Accumulator 314 may operate as a working pressure chamber, and may receive pressured air at a specific pressure and volume from Selector Valve 420 via Delivery Line 403. Sensor 315 may be arranged to monitor the pressure coming from Selector Valve 420 by accessing Delivery Line 403. Sensor 315 may operate to determine the pressure in Delivery Line 403, located between Selector Valve 420 and Accumulator 314 for the purpose of sensing, the level of air pressure, or amount of air pressure available for Accumulator 314 and notifying the host system if the value is too high or too low. Accumulator 314 may provide a specific amount of air pressure at a predetermined volume to Delivery Valve 416 via Delivery Line 404 so that no excess pressure is forced into the Cutter Tubing 318.

PVD Controller 430, in this arrangement configured to interface with a graphical user interface, handpiece or foot pedal control switch, computes a cut rate based on physician input and electronically provides the cut rate to Fixed Pulse Electronics 425 via communications Control Line 407a, which drives Delivery Valve 416 at the specified fixed time cyclical pulse rate via communications Control Line 407a. Although depicted as an integral unit, module 405 functionality may be realized by using an external unit to perform the same functionality as disclosed for the integral unit design. Delivery Valve 416 may open and close in response to the control signal provided from Fixed Pulse Electronics 425. Fixed Pulse Electronics 425 electronically controls the valves operating the regulated pressure sent to the cutter. Fixed Pulse Electronics 425 may connect to Delivery Valve 416 to control Delivery Valve 416. The handpiece blade motion may move in a forward and backward reciprocating motion in response to the pressure waveform generated through Cutting Tubing 318.

During operation, Fixed Pulse Electronics 425 may operate Delivery Valve 416 to deliver a pulse of regulated air pressure to Cutter Tubing 318 and cutter (not shown). The pulses that drive the delivery valve have a fixed width of sufficient duration to drive the cutter to the closed position throughout the entire range of operation. While the surgeon or practitioner may select variations in the pulse repetition frequency, once the selection is made, the pulse width, or width of each pulse, is uniform or constant during handpiece cutter operation.

Fixed Pulse Electronics 425 may electronically control Delivery Valve 416 to transmit pressure in a fixed pulse width and opens and closes at a precise time to allow air at a specific pressure and volume to fill the Cutter Tubing 318 and operate the cutter. Delivery Valve 416 may connect to atmospheric pressure for purposes of venting Cutter Tubing 318. Fixed Pulse Electronics 425 may receive instructions from PVD Controller 430 communicate electronically via communications Control Line 406. PVD Controller 430 may provide an electronic indication to Fixed Pulse Electronics 425 that originates with a user-selected speed, and may be entered via a switch on the handpiece, graphical user interface, or foot switch.

The present design may control the selection of either a low or high range air pressure supply depending on desired cutting speed input from the user. The combination of controlling Selector Valve 420 and Delivery valve 416 via Fixed Pulse Electronics 425 may enable the present design to operate, by varying the pressure or amount of air volume, over a wide range of cutting speeds not available with designs previously available. In this arrangement, the present design may control the amount of pressurized air supplied to the handpiece by varying the supply pressure used based on the desired cutting speed or rate in cuts-per-minute. The present design may involve lower air pressures such that the volume of pressurized air required to be vented or evacuated is reduced, enabling higher cutting rates as the pressure is lowered. The present design can reduce the time required to inject a volume of air needed to advance reciprocating motion of the cutter.

In summary, the present design may control the selector valve to supply the cutter with either of two or more pressures from a variable pressure source or two or more constant pressure sources. The present design entails controlling the delivery valve to either provide an air pressure source or venting and evacuating the cutter tubing.

Figure 5A:
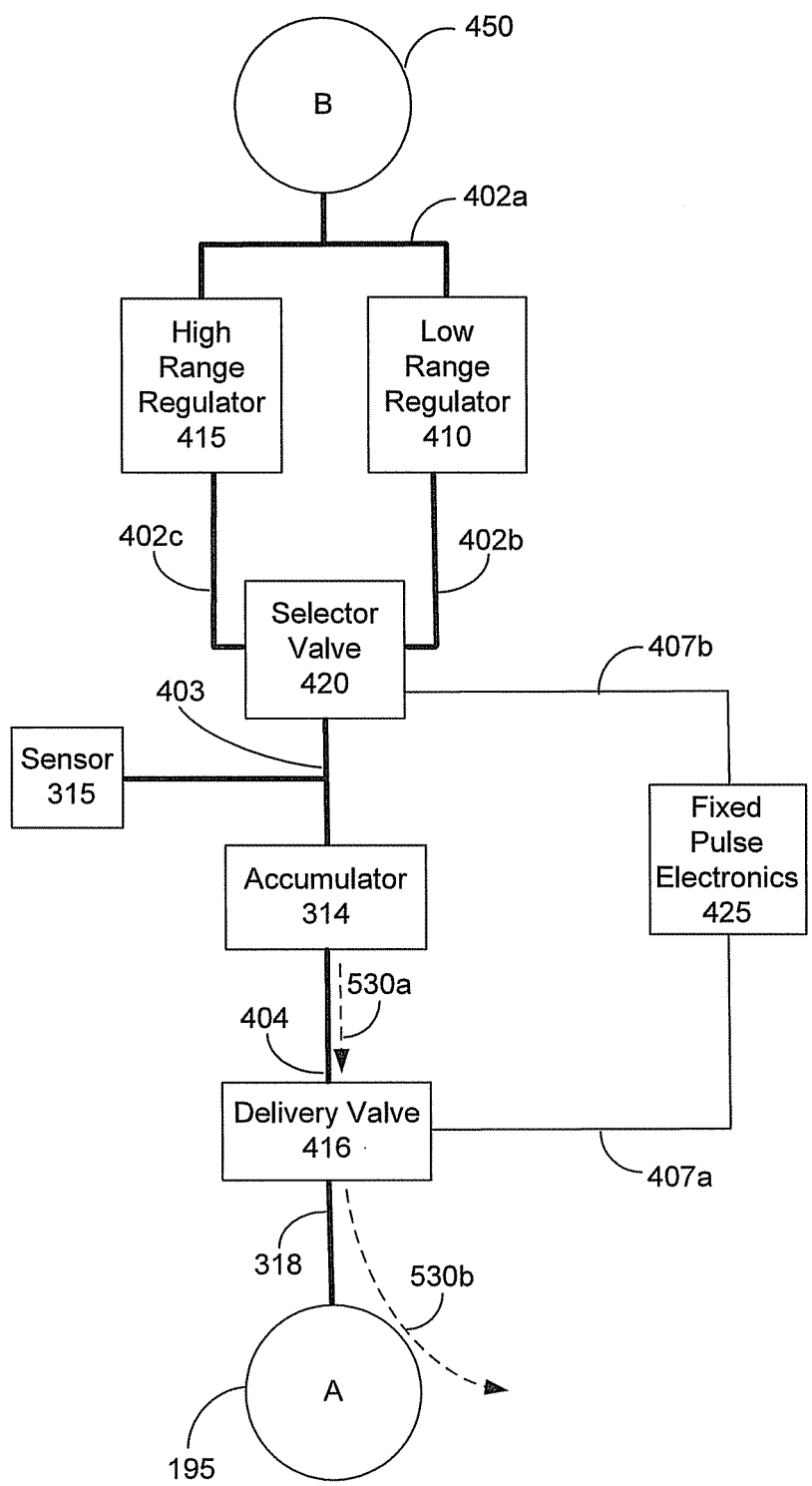
FIG. 5A is a block diagram that shows an example of the present design providing input air pressure supply for driving a blade forward within a vitrectomy handpiece.

FIG. 5A is a block diagram that shows an example of the present design providing input air pressure supply for driving a blade forward within a vitrectomy surgical handpiece. In this example, the present design Fixed Pulse Electronics 425 may switch Selector Valve 420 to the appropriate pressure source in response to user provided cutting speed. The air received from the selected air pressure source is stored in an Accumulator 314 for purposes of driving the cutter. Fixed Pulse Electronics 425 may instruct Delivery Valve 416 to open and close at a predetermined fixed cyclical rate. When Fixed Pulse Electronics 425 instructs Delivery Valve 416 to open, the working supply air pressure stored in Accumulator 314 flows in the direction indicated at 530a through the valve and into the Cutting Tubing 318 as indicated at 530b.

Figure 5B:
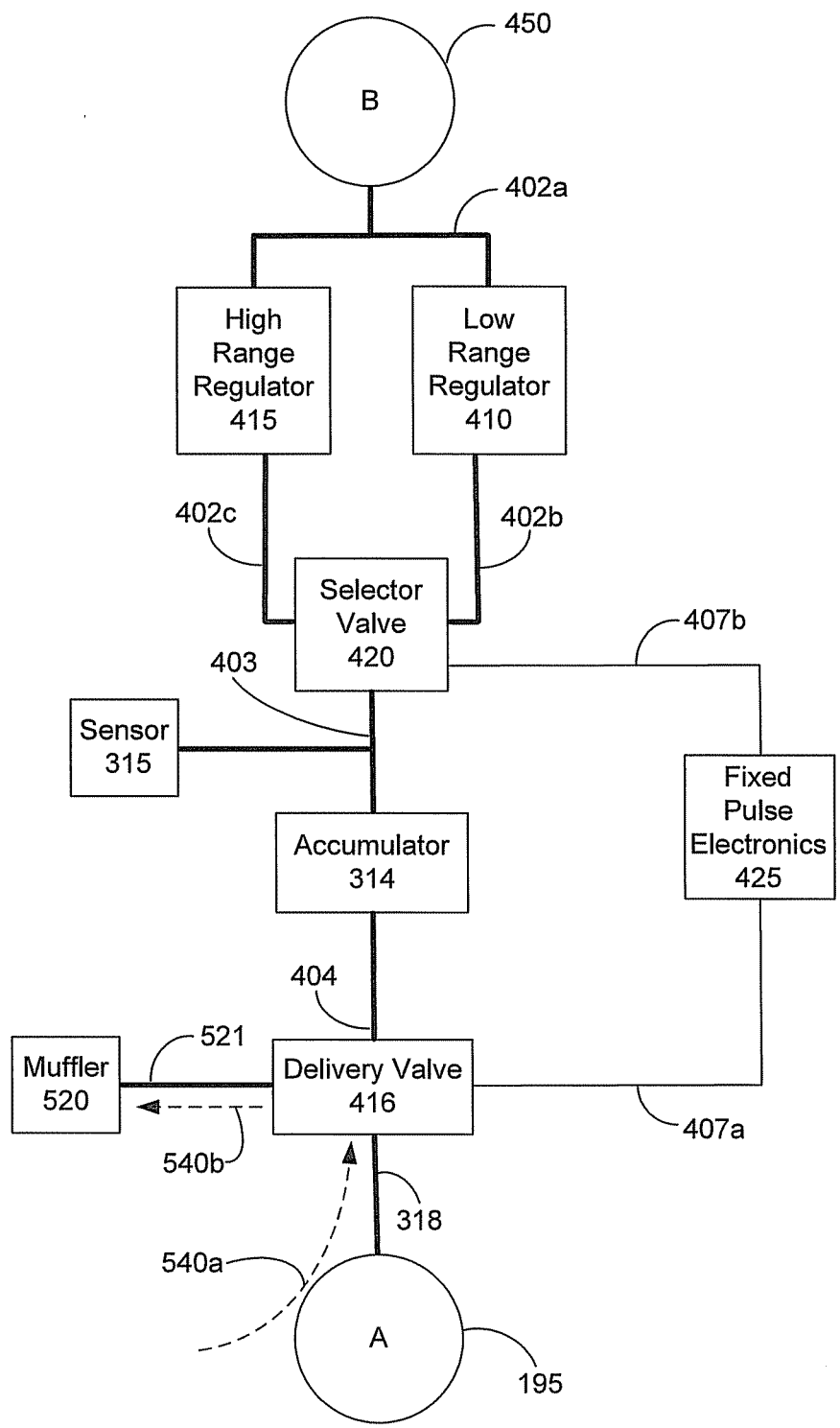
FIG. 5B a block diagram that shows an example of the present design providing output air pressure venting for driving a blade backward within a vitrectomy handpiece.

FIG. 5B a block diagram that shows an example of the present design providing output air pressure venting for driving a blade backward within a vitrectomy surgical handpiece. In this example, once the air pressure burst is supplied from Delivery Valve 416, Fixed Pulse Electronics 425 may instruct Delivery Valve 416 to close. The air received from the previously delivered airbursts are vented or evacuated from Cutting Tubing 318. Closing the delivery valve enables air pressure to flow in the direction indicated at 540a from the cutting tubing back through Delivery Valve 416 and may continue to flow along Delivery Line 521 in the direction indicated at 540b to Muffler 520. Muffler 520 may the vent the received air pressure to the atmosphere.

Fixed Pulse Electronics 425 may provide a set of fixed cyclical instructions to Delivery Valve 416 sufficient to open and close the valve. Each time the present design cycles the valve to it's opened position air pressure flows into the cutting tubing as shown in FIG. 5A. Once the valve has been held opened for the duration indicated by the cyclic instructions, a subsequent instruction commands the valve to close and allow for air to vent through Muffler 520. Moving air pressure in this manner may enable the present design to move the cutting tubing forward and then backward in a cyclic reciprocating motion to effect vitreous material removal.

Figure 6:
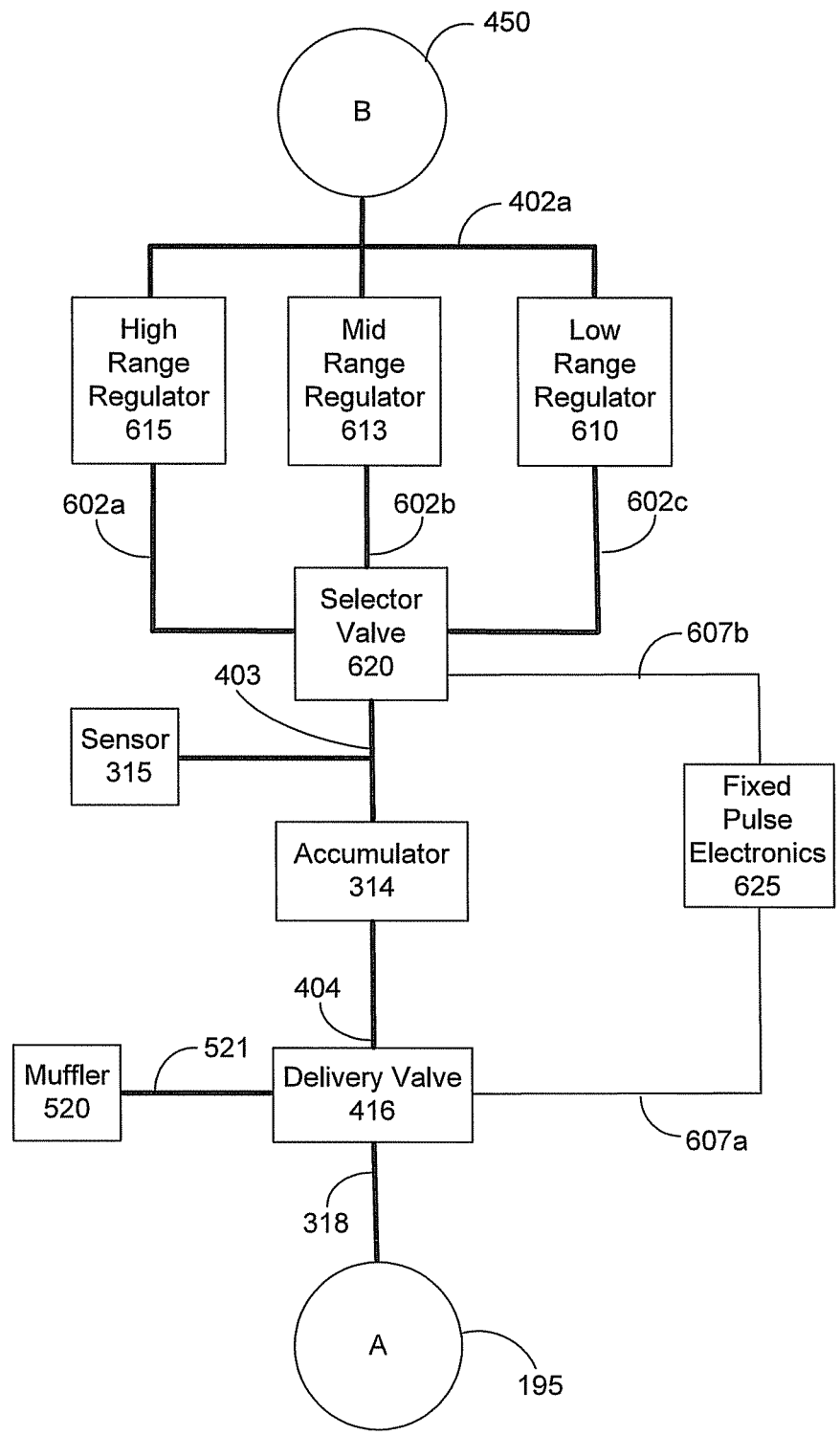
FIG. 6 is a block diagram illustrating three pressure regulators arranged for selection to provide variable input air pressure supply.

FIG. 6 is a block diagram illustrating three pressure regulators arranged for selection to provide variable input air pressure supply in accordance with another aspect of the present invention. In this embodiment of the present design, three regulators are illustrated, although any number of regulators, e.g. 4, 5, or 6, etc., may be accommodated. In this configuration, Selector Valve 620 may switch between three pressure sources, for example high, medium, or low available from either High Range Regulator 615 via Delivery Line 602a, Mid Range Regulator 613 via Delivery Line 602b, or Low Range Regulator 610 via Delivery Line 602c. Once the air pressure source is selected, air pressure received by Selector Valve 620 flows into Accumulator 314 and delivered to Cutting Tubing 318 in the same manner as previously described for the two-pressure regulator configuration. Fixed Pulse Electronics 625 may communicate instructions to Selector Valve 620 via Control Line 607b and communicate instructions to Delivery Valve 416 via Control Line 607a in order to provide cutting tubing 318 with the desired pressure waveform. The number of regulators involved may depend on the lowest and highest desired cutting rates.

Figure 7:
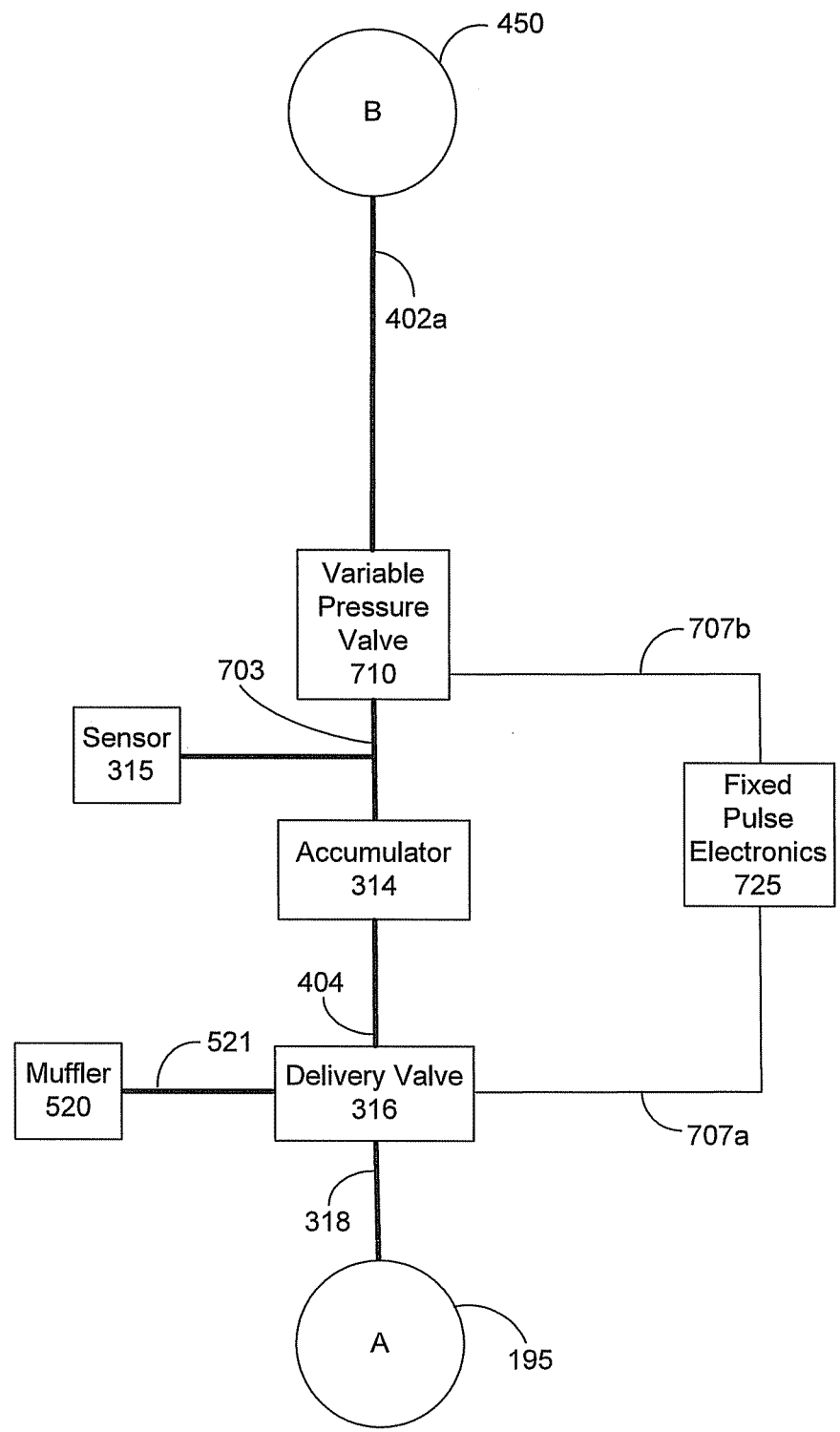
FIG. 7 is a block diagram illustrating an electronically variable pressure regulator configured to change the input air pressure supply.

FIG. 7 is a block diagram illustrating an electronically variable pressure regulator configured to change the input air pressure supply in accordance with another aspect of the present invention. In this embodiment, the present design may involve an electrically variable pressure valve to supply down regulated air pressure to Accumulator 314. In this configuration, Variable Pressure Valve 710 may vary the pressure source through a wide range of pressure values. Once the air pressure set by the user, Fixed Pulse Electronics 725 may send instructions to Variable Pressure Valve 710 over communications Control Line 707b to adjust the valve to required source pressure. Air pressure is supplied by Valve 710 to Accumulator 314 via Delivery Line 703 and delivered to Cutting Tubing 318 in the same manner as previously described for the two-pressure regulator configuration.

Fixed Pulse Electronics 725 may communicate instructions to Selector Valve 710 via Control Line 707b and communicate instructions to Delivery Valve 416 via Control Line 707a in order to provide cutting tubing 318 with the desired pressure waveform. The supported pressure range of Valve 710 may be determined depending on the lowest and highest desired operational cutting rates.

User Interface

A user interface device executing within the Phacoemulsification System 300 communicates with the PVD Controller and provide an input control mechanism for the high-speed vitrectomy cutter. For example, a graphical user interface host system executing within system 300 may provide operational control for the high-speed control mechanism. The user interface device may include, but is not limited to, a touch screen monitor, mouse, keypad, foot pedal switch, and/or a computer monitor. The system 300 may include algorithms and data relating desired cutting speed to required air pressure supply and cycle timing. The algorithms and data may be resident within system 300 or realized using external devices and/or software. Graphical user interfaces are generally known in the art, and the graphical user interface may provide, for example, touch screen or button selectability of desired pressure(s) by the user touching the screen or pressing buttons on the interface. Other user interfaces may be provided, such as a selection device including but not limited to a foot pedal switch as discussed.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. An apparatus configured to control cutting speed of a cutting device employable in an ocular surgical procedure, comprising:
   a control module;
   a variable gas pressure regulator arrangement configured to receive gas from a gas pressure supply, wherein said variable gas pressure regulator arrangement is connected to the control module and the control module is configured to regulate gas received from the gas pressure supply, the variable gas pressure regulator arrangement comprising a selector valve configured to receive pressure selected from a high range regulator and a low range regulator arranged in parallel; and
   an accumulator configured to store gas received from the variable regulator arrangement at a selected gas pressure;
   wherein gas at the selected gas pressure is delivered from said accumulator to said cutting device.

2. The apparatus of claim 1, wherein the cutting device receives gas from said accumulator when a delivery valve is open, and vents gas when said delivery valve is closed.

3. The apparatus of claim 2, wherein said control module is configured to generate a fixed timing cyclical pulse waveform signal to open and close said delivery valve.

4. The apparatus of claim 1, wherein the control module comprises a sensor configured to monitor a gas pressure source value during operation of the apparatus.

5. An apparatus configured to control cutting speed of a cutting device employable in an ocular surgical procedure, comprising:
   a high range regulator and a low range regulator arranged in parallel and configured to receive gas from a gas pressure supply;
   a selector valve configured to receive and provide pressure selected from one of the high range regulator and the low range regulator; and
   an accumulator configured to store gas received from the selector valve at a selected gas pressure;
   wherein gas at the selected gas pressure is delivered from said accumulator to said cutting device.

6. The apparatus of claim 5, wherein the cutting device receives gas from said accumulator when a delivery valve is open, and vents gas when said delivery valve is closed.

7. The apparatus of claim 5, further comprising a control module, wherein the control module comprises a sensor configured to monitor a gas pressure source value during operation of the apparatus.

8. The apparatus of claim 6, further comprising a control module, wherein said control module is configured to generate a fixed timing cyclical pulse waveform signal to open and close said delivery valve.

* * * * *